(12) United States Patent
Thiruvengadam et al.

(10) Patent No.: US 6,207,822 B1
(45) Date of Patent: Mar. 27, 2001

(54) PROCESS FOR THE SYNTHESIS OF AZETIDINONES

(75) Inventors: Tiruvettipuram K. Thiruvengadam, Kendall Park; Xiaoyong Fu, Edison; Chou-Hong Tann, Berkeley Heights; Timothy L. McAllister, Westfield; John S. Chiu, Parsippany; Cesar Colon, Rahway, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/455,482

(22) Filed: Dec. 5, 1999

Related U.S. Application Data

(60) Provisional application No. 60/111,249, filed on Dec. 7, 1998.

(51) Int. Cl.[7] .................... C07D 205/08; C07D 263/26
(52) U.S. Cl. ................................. 540/200; 548/230
(58) Field of Search .......................... 540/200; 548/230

(56) References Cited

U.S. PATENT DOCUMENTS

| 5,561,227 | 10/1996 | Thiruvengadam et al. | 540/200 |
| 5,631,365 | 5/1997 | Rosenblum | 540/200 |
| 5,728,827 | 3/1998 | Thiruvengadam et al. | 540/200 |

(List continued on next page.)

OTHER PUBLICATIONS

"Kirk–Othmer Concise Encyclopedia of Chemical Technology", Grayson, Martin Ed., 1985, John Wiley, New York, p. 1065–1066

(List continued on next page.)

*Primary Examiner*—Mukund J. Shah
*Assistant Examiner*—Thomas C McKenzie
(74) *Attorney, Agent, or Firm*—Anita W. Magatti

(57) ABSTRACT

This invention provides a process for preparing the hypocholesterolemic compound

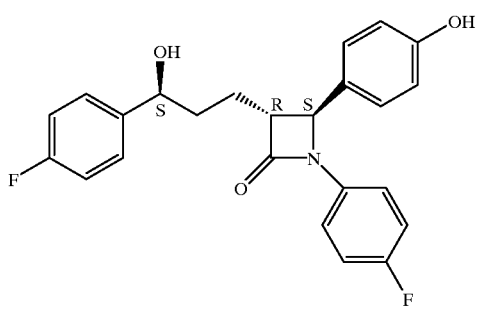

comprising:

(a) reacting p-fluorobenzoylbutyric acid with pivaloyl chloride and acylating the product with a chiral auxiliary to obtain a ketone of formula IV:

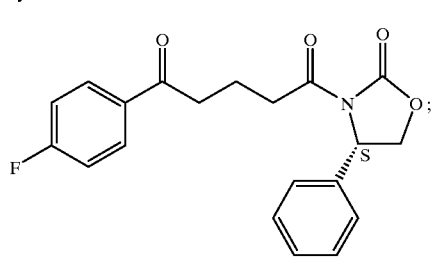

(b) reducing the ketone of formula IV in the presence of a chiral catalyst to an alcohol:

(c) reacting the chiral alcohol of step (b), an imine and a silyl protecting agent, then condensing the protected compounds to obtain a β-(substituted-amino)amide of formula VII:

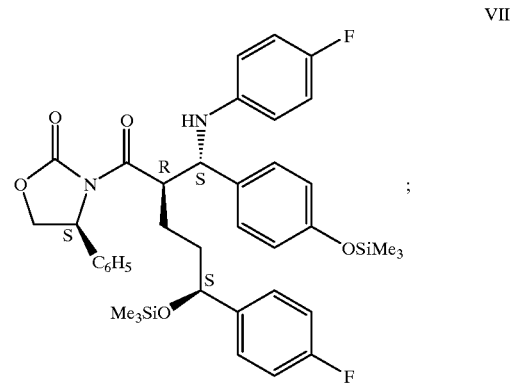

(d) cyclizing the β-(substituted-amino)amide of formula VII with a silylating agent and a fluoride ion catalyst to obtain a protected lactam of the formula VIII:

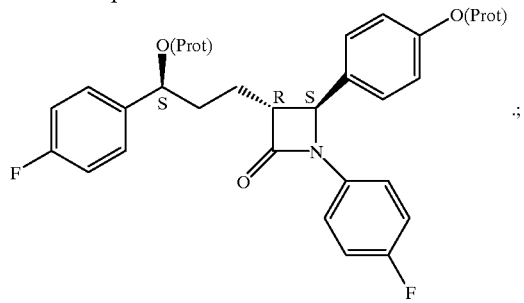

and removing the protecting groups.

The intermediates of formulas VII and VIII are also claimed.

17 Claims, No Drawings

U.S. PATENT DOCUMENTS

| | | | |
|---|---|---|---|
| 5,739,321 | 4/1998 | Wu et al. | 540/200 |
| 5,767,115 | 6/1998 | Rosenblum et al. | 514/210 |
| 5,856,473 | 1/1999 | Shankar | 540/200 |

OTHER PUBLICATIONS

Greene, T. W. and Wuts, P.G.M., "Protecting Groups in Organic Synthesis, 3rd Edition", 1995, John Wiley, New York, p. 113–121.

PROCESS FOR THE SYNTHESIS OF AZETIDINONES

CROSS REFERENCE TO RELATED APPLICATIONS

This application claims the benefit of U.S. Provisional Application Ser. No. 60/111,249 filed on Dec. 7, 1998.

BACKGROUND

This invention relates to an enantioselective process for producing hydroxy-alkyl substituted azetidinones useful as hypocholesterolemic agents, in particular for preparing 1-(4-fluorophenyl)-3(R)-[3(S)-hydroxy-3-(4-fluorophenyl) propyl)]-4(S)-(4-hydroxyphenyl)-2-azetidinone, claimed in U.S. Pat. No. 5,767,115.

Processes for preparing the corresponding azetidinone without the 3-hydroxy substitutent are claimed in U.S. Pat. Nos. 5,728,827 and 5,561,227. Other processes for preparing 1-(4-fluorophenyl)-3(R)-[3(S)-hydroxy-3-(4-fluorophenyl)-propyl)]-4(S)-(4-hydroxyphenyl)-2-azetidinone are disclosed in U.S. Pat. Nos. 5,631,365 and 5,739,321.

SUMMARY OF THE INVENTION

This invention provides an improved simple, high-yielding process using neutral conditions for producing the hypocholesterolemic azetidinone having the formula I

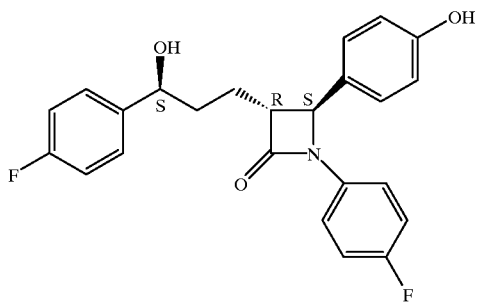

comprising:

(a) reacting p-fluorobenzoylbutyric acid of formula II with pivaloyl chloride and acylating the product with a chiral auxiliary of formula III to obtain a ketone of formula IV:

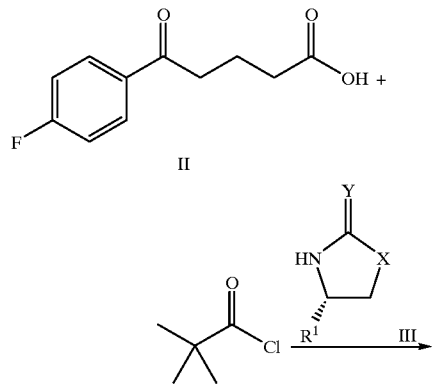

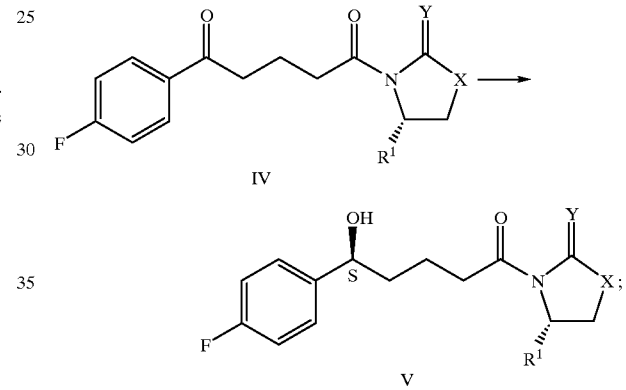

wherein X is —O—, —S— or —N($C_1$–$C_6$ alkyl); Y is =O or =S; and $R^1$ is $C_1$–$C_6$ alkyl, phenyl, naphthyl, substituted phenyl, substituted naphthyl, $C_1$–$C_6$ alkoxycarbonyl or benzyl, wherein the substituents on phenyl and naphthyl are 1–3 substituents selected from the group consisting of $C_1$–$C_6$ alkyl, phenyl and benzyl;

(b) reducing the ketone of formula IV in the presence of a chiral catalyst to an alcohol of formula V:

(c) reacting the chiral alcohol of formula V, an imine of formula VI and a silyl protecting agent, then condensing the silyl-protected compounds to obtain a β-(substituted-amino)amide of formula VII, wherein Prot is a silyl protecting group:

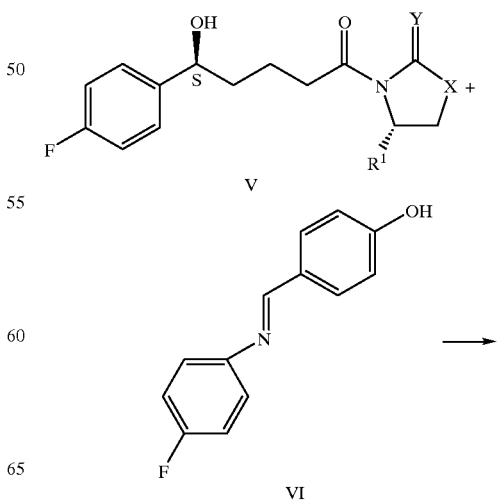

3
-continued

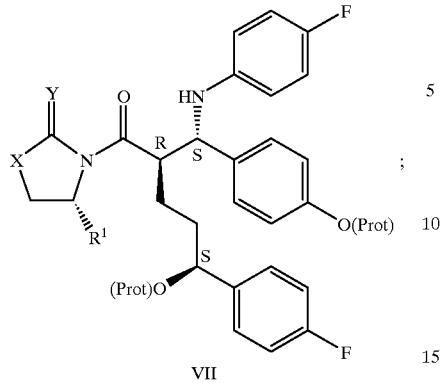

(d) cyclizing the β-(substituted-amino)amide of formula VII with
  (i) a silylatinrg agent and a fluoride ion catalyst cyclizing agent;
  (ii) a silylating agent and a quaternary ammonium salt of a chiral auxiliary of formula III; or
  (iii) a strong non-nucleophlic base;
to obtain the compound of formula VIII:

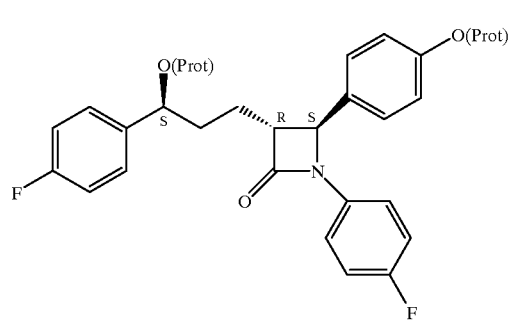

(e) removing the silyl protecting groups.

Also claimed are the process comprising steps (c), (d) and (e); the process of steps (d) and (e); the process of step (c); and the process of step (d), particularly the cyclization described in step (d)(i).

In still another aspect, the intermediates of formula VII and VIII are claimed.

The process described above is directed to the preparation of the 1-(4-fluorophenyl)-3(R)-[3(S)-hydroxy-3-(4-fluorophenyl)propyl)]-4(S)-(4-hydroxyphenyl)-2-azetidinone enantiomer, but it will be recognized that by substitution of the appropriate starting materials, other enantiomers can be prepared.

DETAILED DESCRIPTION

The process of this invention is a high throughput process which provides the desired azetidinone in high overall yield in a short time cycle (i.e., about two weeks).

Preferred reaction conditions are shown in the following scheme:

Step (a):

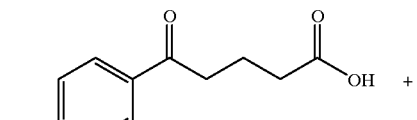

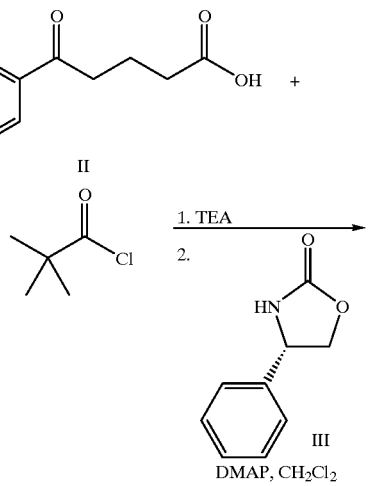

Step (b):

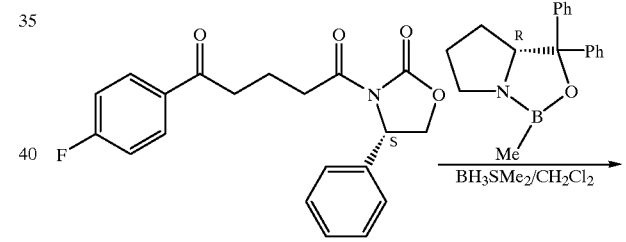

Step (c):

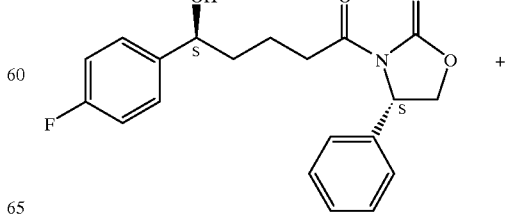

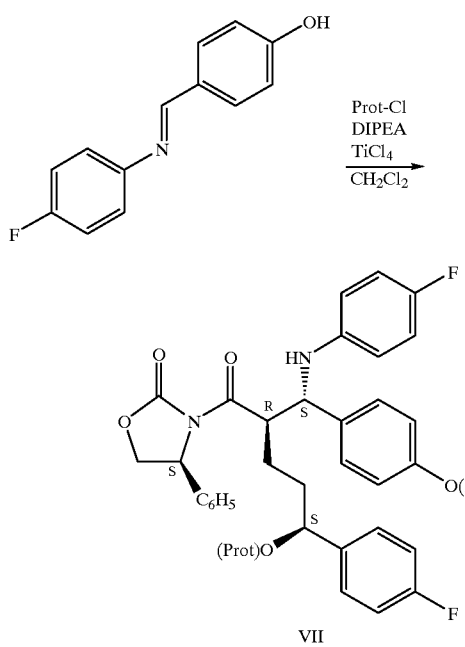

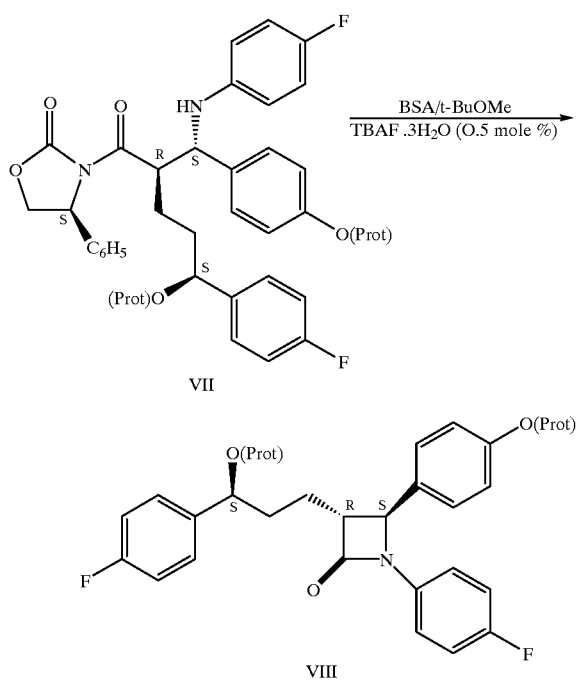

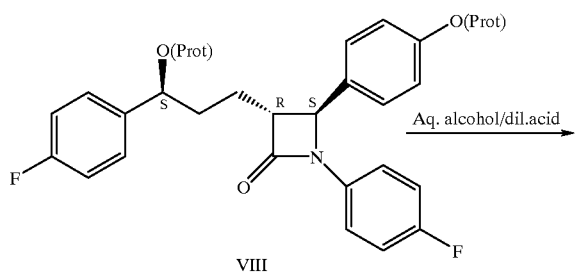

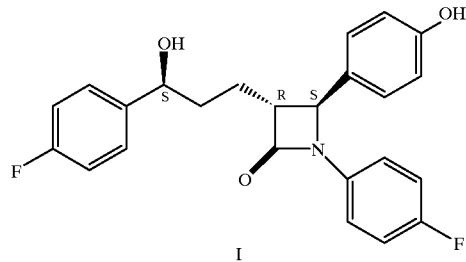

In the reaction scheme, TEA is triethylamine, DMAP is 4-dimethyl-amino pyridine, DIPEA is diisopropylethylamine, BSA is bistrimethylsilyl acetamide, TBAF is tetra n-butyl-ammonium fluoride, t-BuOMe is t-butyl methyl ether and Prot is a silyl protecting group as defined below.

Starting materials of formulas II and III are known in the art, and the procedure of step (a) for reacting compounds of formula II and III is known in the art: Preferably, the chiral auxiliary of formula III is exemplified by the formula:

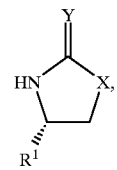

wherein Y is =O, X is —O— and $R^1$ is phenyl, benzyl or $C_1$–$C_6$ alkyl. A preferred chiral auxiliary is

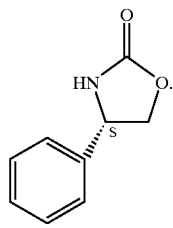

See the example below for typical reaction conditions.

Similarly, the procedure of step (b) for reducing a ketone to a hydroxy group using a borane reducing agent such as $BH_3 \cdot (CH_3)_2$ in the presence of a chiral catalyst such as (R)-tetrahydro-1-methyl-3,3-diphenyl-1H,3H-pyrrolo(1,2-c)(1,3,2) oxaza-borolidine is known: see U.S. Pat. No. 5,767,115.

In step (c), the chiral alcohol, V, and the imine, VI, are protected with a suitable hydroxy-protecting group, preferably a silyl protecting group such as that derived from chlorotrimethylsilane (TMSCl) or t-butyldimethyl-silyl chloride (TBDMSCl). The alcohol (1 equivalent) and imine (preferaby 1–3 equivalents) are added to an anhydrous solvent such as $CH_2Cl_2$, the reaction mixture is cooled to −10° to 150° C., a tertiary amine base such as DIPEA is added (preferably 2–4 equivalents), and sufficient silylating reagent to react with both the alcohol and the imine is added (e.g., 2–4 equivalents). After silylation is complete, the alcohol and imine are condensed by reacting at −20° to −35° C. with at least 1 equivalent of a Lewis acid such as $TiCl_4$, in the presence of a tertiary amine base (preferably 1–3 equivalents) such as DIPEA for 2–4 hours. The reaction is quenched, for example by treating with an acid such as glacial acetic acid followed by aqueous tartaric acid solution; the resultant product is extracted and crystallized using conventional procedures.

Silylation in step (d) is effected by reacting the compound of formula VII with a silyl-enol ether silylating agent such as bistrimethylsilyl acetamide (BSA), N-methyl-O-trimethylsilyl acetamide or iso-propenyloxy trimethylsilane, preferably BSA, in a suitable inert organic solvent at −20° C. to 110° C., preferably at about 0° C. to 25° C. The reaction is preferably carried out in a dry, inert atmosphere, e.g., the solvent is dried, typically with molecular sieves, and the reaction is carried out under nitrogen.

The order of addition of the components of this process in Step (d) is not critical to the preparation of the azetidinone product. For example, the β-(substituted-amino)amide can first be reacted with the silylating agent and then reacted with the cyclizing agent, or the compound of formula VII can be added to a mixture of the silylating agent and the cyclizing agent. When the silylation and cyclization are done sequentially, i.e., the silylating agent is reacted with the starting material first, the silylation reaction can be allowed to continue for up to about two hours, but preferably the cyclization step is carried out immediately after silylation, or the silylating agent and the cyclizing agent are added simultaneously.

The source of the fluoride ion used to catalyze the intra-molecular cyclization of the compound of formula VII is typically a quaternary alkyl-, aryl-alkyl- or arylalkyl-alkylammonium fluoride salt or a hydrate thereof, or a mixture thereof, or is an alkali metal fluoride salt or a hydrate thereof, such as cesium fluoride or potassium fluoride. Examples of arylalkyl-alkyl-ammonium groups are benzyltriethyl-ammonium and benzyltrimethyl-ammonium; examples of arylalkyl-ammonium are phenyltriethyl-ammonium and phenyltrimethyl-ammonium; typical alkylammonium groups contain alkyl groups of 1–6 carbon atoms, e.g., tetra n-butyl-ammonium. When a hydrated quaternary ammonium fluoride salt is used, the reagent is added in a catalytic amount, i.e., about 0.1 to about 20 mole percent, preferably about 0.5 to 5 mole percent, and when an anhydrous quaternary ammonium fluoride salt is used, it can be added in a catalytic up to a stoichiometric amount. When an alkali metal fluoride salt is used, it is added in catalytic amount up to a stoichiometric amount compared to the starting β-amino compound, depending on the solubility of the reagent in the solvent used (higher solubility requires less reagent). If added to the reaction mixture after the silylation agent, the fluoride reagent is added directly to the reaction mixture resulting from silylation, and is reacted at about 0° C. to 110° C., preferably about 0° C. to 50° C., for about 0.5 to about 6 hours, preferably about 2 hours. When the silylation reagent and the fluoride reagent are added simultaneously, the reaction is conducted under similar conditions. A preferred fluoride ion catalyst cyclizing agent is tetrabutylammonium fluoride trihydrate.

Alternatively, the cyclization of step (d) can be effected by the addition of a monovalent quaternary ammonium salt of the chiral auxiliary of formula III used in step (a), i.e., a compound of the formula

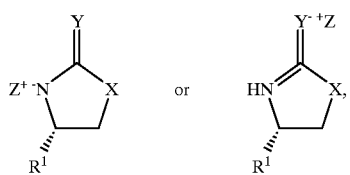

wherein X, Y and $R^1$ are as defined above and Z is a quaternary ammonium cation selected from the group consisting of arylalkyl-alkylammonium, aryl-alkylammonium and tetraalkylammonium, or a mixture thereof, and alkali metals. Examples of arylalkyl-alkylammonium are benzyl-triethylammonium and benzyl-trimethylammonium; examples of aryl-alkylammonium are phenyltriethylammonium and phenyltrimethyl-ammonium; typical tetraalkylammonium groups contain alkyl groups of 1–6 carbon atoms, e.g., tetra n-butylammonium; and typical alkali metals are sodium, potassium, cesium and lithium. Other chiral or non-chiral auxiliaries can also be used to cyclize the β-(substituted-amino)amide of formula VII, for example compounds of the formulas

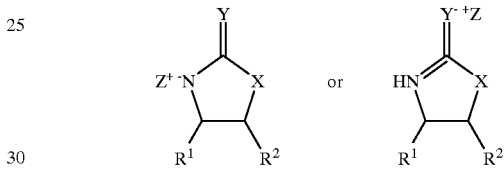

wherein X, Y, Z and $R^1$ are as defined above and $R^2$ is defined as for $R^1$ can also be used. The the β-(substituted-amino)amide of formula VII is treated with a silylating agent as described above, with the salt of the chiral (or non-chiral) auxiliary being added either simultaneously or sequentially in a catalytic or stoichiometric amount compared to the β-amino compound under conditions similar to the reaction with fluoride ion.

A third method for cyclizing the β-(substituted-amino) amide of formula VII comprises using a strong non-nucleophilic base. A strong non-nucleophilic base is defined herein as a non-aqueous base which does not act as a nucleopile by virtue of its steric bulk, e.g., sodium bistrimethylsilylamide or lithium diisopropylamide. The base is reacted with the the β-amino compound in an inert organic solvent such as $CH_2Cl_2$ at a temperature of about −100° C. to 10° C.

Removal of the protecting groups after cyclization is carried out using conventional methods, for example by treatment with a dilute acid such as sulfuric acid in a solvent such as an alcohol, e.g., isopropanol.

Intermediates IV and VII can be isolated during the reaction process, or the reaction can proceed to formation of the compound of formula I before the product is isolated.

The azetidinone resulting from the cyclization can be purified by appropriate standard procedures such as crystallization or column chromatography.

The term "suitable inert organic solvent" as used above means any organic solvent or combination of solvents that is unreactive in the reaction being conducted and is a solvent for the reactants. Typical suitable solvents are halogenated compounds such as $CH_2Cl_2$; heterocyclic compounds such as tetrahydrofuran (THF); DMSO; dimethylformamide (DMF); acetonitrile; carbocyclic aromatics such as toluene; and t-BuOMe. Preferred are t-BuOMe, $CH_2Cl_2$, toluene and THF.

Those skilled in the art will recognize that for cyclization of step (d) to proceed as desired, the —OH substituents present in the intermediates of formulas V and VI used in step (c) must be protected prior to cyclization, hence the treatment in step (c) with a hydroxy-protecting group. A key feature of this process is the surprising stability of the silyl protecting groups on the carbinol and phenol moieties in both step (c) and step (d). In step (c), after the reaction of intermediates V and VI, the reaction is quenched with acid, preferably acetic acid and aqueous tartaric acid: the resulting solution has a pH<1. Under these conditions, one would not predict that the disilylated compound of formula VII (containing a silylated phenolic group) would be stable, but surprisingly the compound is stable and can be isolated for use in the next step of the process. Also, in step (d) of the process of the invention, out of the three silylated groups (i.e., the two hydroxy groups silylated in step (c) and the —NH— group silylated in the first part of step (d)), the —N—Si— group is selectively desilylated, allowing the intramolecular cyclization to proceed efficiently. This was unpredictable, especially in view of the presence of a silylated phenol group.

The following example illustrates the process of this invention.

Step (a):

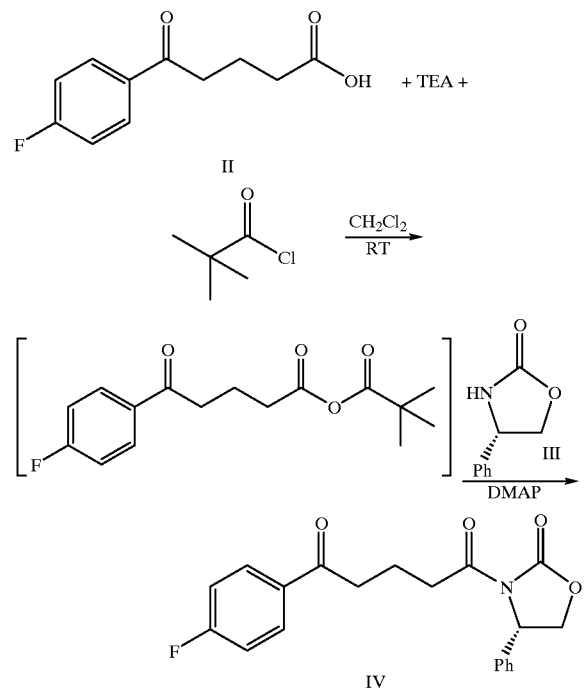

Equip a 3-necked 500 mL round bottom flask with a thermometer, an addition funnel and a nitrogen inlet. Add p-fluoro-benzoylbutyric acid (20 g, 95.15 mmol), $CH_2Cl_2$ (100 mL) and TEA (23 mL, 165 mmol) and agitate the mixture at room temperature for 5 min. Add trimethylacetyl chloride (11.3 mL, 91.75 mmol) slowly over a period of 30 min. Check for complete formation of mixed anhydride by NMR.

Add the compound of formula III (10 g, 61.3 mmol), DMAP (1.6 g, 13 mmol) and dry DMF (10 mL) and heat the mixture at reflux for about 7 h or until the reaction is complete (<3% compound III) by NMR. Cool to room temperature, transfer the batch to a flask containing 2N $H_2SO_4$ (80 mL) slowly with agitation and continue agitation for about 30 min. Separate the layers and wash the organic layer with 5% $NaHCO_3$ (80 mL).

Concentrate the organic layer and crystallize the product from isopropyl alcohol (100 mL), filter and dry. Yield: 20 (92% molar); mp: 92–94° C.

Step (b):

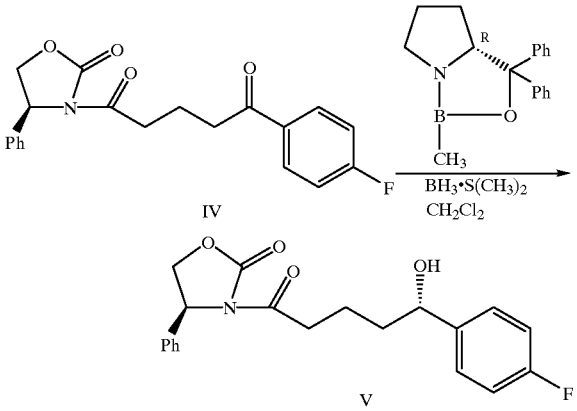

Equip a 3-necked 250 mL round bottom flask with a thermometer, an addition funnel and a nitrogen inlet. Add dry $CH_2Cl_2$ (20 mL) and neat borane dimethyl sulfide (2.82 mL, 28.2 mmol) and cool the mixture to −5° to 0° C. Add a previously prepared toluene solution of (R)-tetrahydro-1-methyl-3,3-diphenyl-1H,3H-pyrrolo(1,2-c)(1,3,2) oxaza-borolidine (1.4 mL, 1.4 mmol, 5 mole %) to the mixture and stir for 15 min. at <0° C. Add a solution of compound IV(10 g, 28.1 mmol) in $CH_2Cl_2$ (30 mL) slowly over a period of 3–4 h and maintain the reaction temperature between −5° to 0° C. Continue stirring for 1 to 2 h or until the reaction complete (<0.1% compound IV) by NMR. Quench the reaction by slowly adding $CH_3OH$ (4 mL) while maintaining the temperature <0° C. Add 5% hydrogen peroxide (20 mL) followed by 4N $H_2SO_4$ (1.5 mL). Agitate the mixture for 15 min., separate the organic layer and wash with 2N $H_2SO_4$ (20 mL), 5% $Na_2SO_3$ (50 mL) and 10% NaCl (50 mL). Concentrate the organic layer to a low volume until water content is <0.05%. The product is used directly in the next step. Solution yield: >95%; de: 98%.

Step (c):

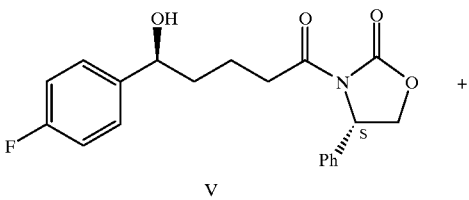

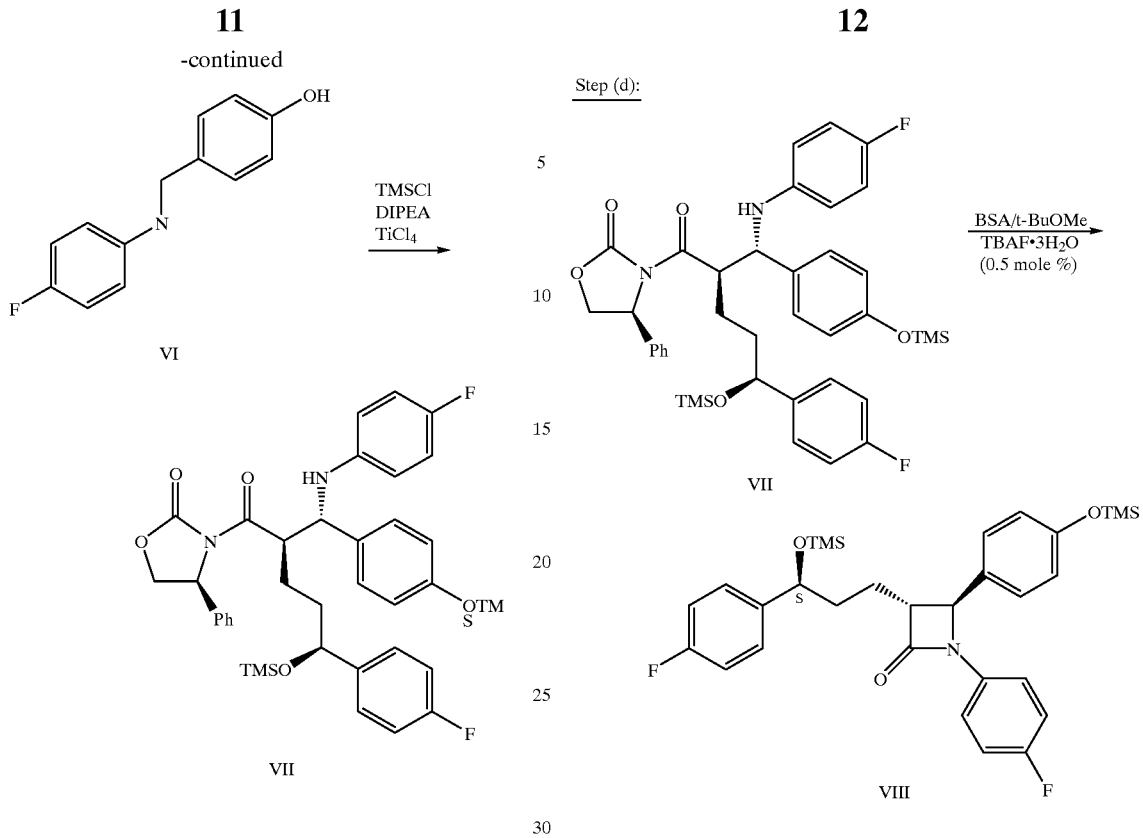

Equip a 3-necked 500 mL round bottom flask with a thermometer, an addition funnel and a nitrogen inlet. Add the CH$_2$Cl$_2$ solution of compound V (10 g equivalent of compound IV, 28.1 mmol) from step (b) and compound VI (12.05 g) and adjust the total volume of the reaction mixture to 150 mL with dry CH$_2$Cl$_2$. Cool the mixture to –10° C. and add slowly DIPEA (25.7 mL, 147.5 mmol) and maintain the temperature at <–5° C. Add TMSCl (13.5 mL, 92.3 mmol) over a period of 30 min. while maintaining the reaction temperature <–5° C. Agitate the reaction for 1 h or until the silylation is judged complete by NMR. Lower the reaction temperature to –25 to –30° C. Add TiCl$_4$ (3.4 mL, 30.8 mmol) slowly and maintain the temperature <–25° C. Agitate the reaction for 3 h at <–25° C. and check the reaction completion by NMR. Add glacial acetic acid (8 mL) slowly to the reaction mixture while maintaining the reaction temperature between –25 and –30° C. Pour the reaction mixture into 7% aqueous tartaric acid solution (140 mL) at 0° C., agitate for 1–2 h, and allow the temperature to gradually rise to room temperature. Add 20% aqueous NaHSO$_3$ solution (50 mL) and continue agitation for another 2 h. Separate the organic layer and wash with water (120 mL). Concentrate the organic layer to a low volume and add bistrimethylsilyl acetamide (8.4 mL) and heat the mixture to reflux for 30 min. Concentrate the mixture to remove CH$_2$Cl$_2$ and crystallize the product from an ethyl acetate and heptane mixture, filter, wash and dry to give 13 g (65% molar yield from compound IV) of compound VI.

Equip a 3-necked 500 mL round bottom flask with a thermometer, an addition funnel and a nitrogen inlet. Add compound VII (50 g, 69.7 mmol), tetrabutylammonium fluoride trihydrate (0.1 g, 0.32 mmol), bistrimethyl acetamide (30 mL) and t-butylmethyl ether (500 mL). Stir the mixture at room temperature for 2 h or until the reaction is judged complete by NMR. Add glacial acetic acid (2.5 mL) and concentrate the reaction mixture to an oil under vacuum.

Step (e)

Add a premixed solution of isopropyl alcohol (250 mL) and 2N H$_2$SO$_4$ (25 mL) to the product of step (d) and agitate the mixture at room temperature for 1 h. Crystallize compound I from aqueous isopropyl alcohol. Filter the product and wash with dilute aqueous isopropyl alcohol followed by water until the pH of wash is <5. Dry the product at 60° C. in a draft oven or under vacuum to give 26.14 g (91.5% molar yield) of compound I.

Starting materials for the claimed process are made by the following typical procedures.

Preparation of 4-(4-fluorobenzoyl)butyric acid:

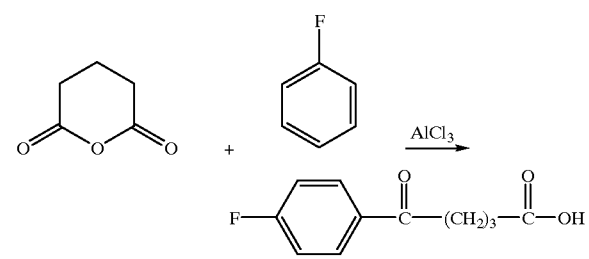

Charge 250 g of anhydrous AlCl₃ (1.87 moles) to a 2 L 3-neck round bottom flask, add 300 mL fluorobenzene (307.5 g; 3.2 moles) and cool the mixture in an ice bath to 5° C. Add a hazy suspension of 100 g glutaric anhydride (0.86 mole) in 400 mL fluorobenzene (4.3 moles) through an addition funnel over a period of 45 min., and maintain the temperature below 12° C. Warm the reaction mixture to ambient temperature gradually and agitate at r.t. for about 90 min.; check for completion by NMR. Cool the reaction mixture to 0 to 5° C., then add a cold aqueous solution (700 mL) of 1N HCl carefully to the mixture to destroy any unreacted AlCl₃, keeping the temperature of the mixture below 20° C. during the early part of the acid addition, and below 40° C. for the rest of the time. Pour the entire mixture into a 2 L 1:1 mixture of water and ice (v/w) to precipitate out crude products, filter the white suspension and wash well with water. Add the white residue to 3 L of aqueous saturated solution (~5%) of NaHCO₃, heat the basic mixture on a steam bath for one hour and filter the batch while hot through a thin pad of celite. Cool the filtrate to r.t., add about 320 mL of concentrated HCl dropwise into the filtrate to pH 1 to crystallize out products, and agitate the white suspension in an ice bath for 30 min. Filter the batch, wash the wet cake with ice cold water and dry in a vacuum oven at 50° C. for 16 h to obtain 143.2 g of 4-(4-fluorobenzoyl)-butyric acid; m.p. 141 to 142° C., isolated yield: 79.3%.

Preparation of Imine

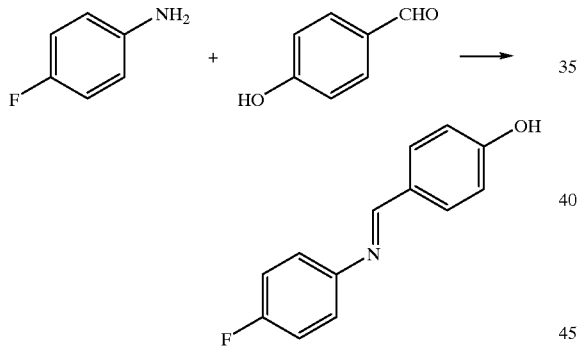

Equip a three necked 1 L flask with a mechanical stirrer, thermometer and an addition funnel. Add 480 mL of isopropanol, 144 g (1.18 moles) of p-hydroxybenzaldehyde (endothermic) and agitate the mixture while heating to a temperature of 50° C. Agitate the mixture at 50° C. for 15 min (making sure all the material is in solution), then add 114 mL (1.2 moles) of p-fluoroaniline slowly via the addition funnel (exothermic reaction). After the addition is complete, agitate the thick slurry for 1 hr at 50° C., cool to r.t. and agitate for 30 min. Filter the product, wash the cake with 150 mL of isopropanol, dry the wet cake in a draft oven at 50° C. for 24 h or until dry to yield 222 g of the imine (88%); mp: 180–182° C.

We claim:

1. A process for preparing a compound represented by the formula

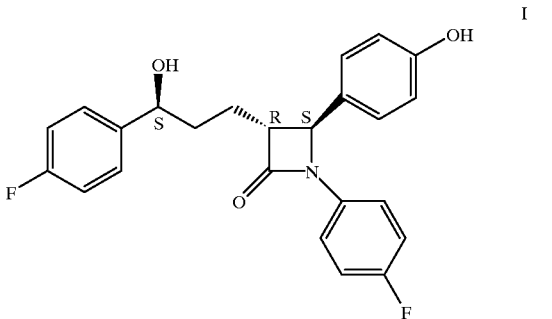

comprising:

(a) reacting p-fluorobenzoylbutyric acid of formula II with pivaloyl chloride and acylating the product with a chiral auxiliary of formula III to obtain a ketone of formula IV:

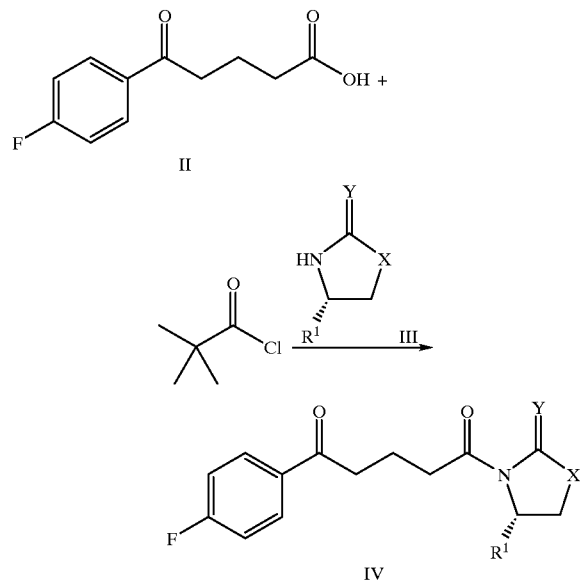

wherein X is —O—, —S— or —N(C₁–C₆ alkyl); Y is =O or =S; and R¹ is C₁–C₆ alkyl, phenyl, naphthyl, substituted phenyl, substituted naphthyl, C₁–C₆ alkoxycarbonyl or benzyl, wherein the substituents on phenyl and naphthyl are 1–3 substituents selected from the group consisting of C₁–C₆ alkyl, phenyl and benzyl;

(b) reducing the ketone of formula IV in the presence of a chiral catalyst to an alcohol of formula V:

-continued

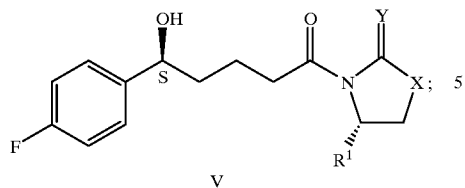

V (c) reacting the chiral alcohol of formula V, an imine of formula VI and a hydroxy protecting agent, then condensing the hydroxy-protected compounds to obtain a β-(substituted-amino)amide of formula VII, wherein Prot is a hydroxy protecting group:

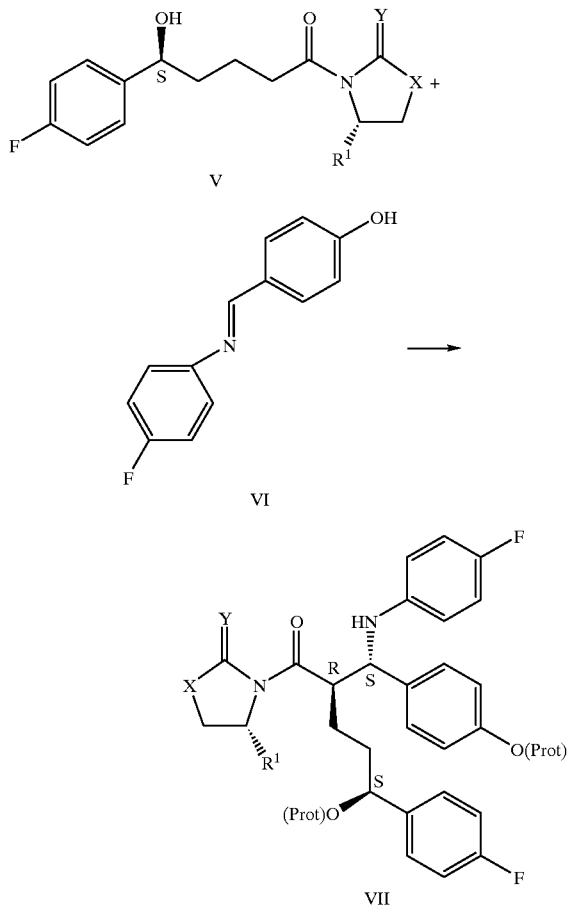

(d) cyclizing the β-(substituted-amino)amide of formula VII with
  (i) a silylating agent and a fluoride ion catalyst cyclizing agent;
  (ii) a silylating agent and a quaternary ammonium salt of a chiral auxiliary of formula III; or
  (iii) a strong non-nucleophlic base;

to obtain the compound of formula VIII:

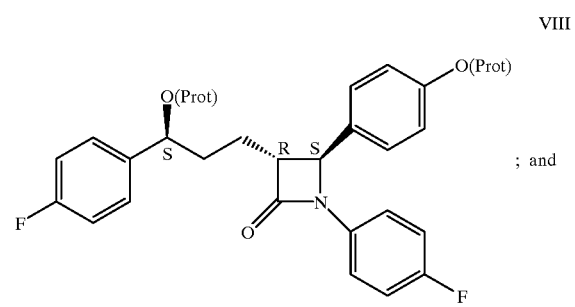

(e) removing the hydroxy protecting groups.

2. The process of claim 1 wherein in step (d), the cyclization is effected with a silylating agent and a fluoride ion catalyst.

3. The process of claim 1 wherein in step (a), the chiral auxiliary is (4S)-4-phenyl-2-oxazolidinone.

4. The process of claim 1 wherein in step (b) the chiral catalyst is (R)-tetrahydro-1-methyl-3,3-diphenyl-1H,3H-pyrrolo(1,2-c)(1,3,2) oxaza-borolidine.

5. The process of claim 1 wherein in step (c) the hydroxy protecting agent is chlorotrimethylsilane and the condensation is effected with a Lewis acid in the presence of a tertiary amine.

6. The process of claim 1 wherein in step (d) the silylating agent is bistrimethylsilyl acetamide and the fluoride ion catalyst cyclizing agent is tetrabutylammonium fluoride trihydrate.

7. The process of claim 2 wherein in step (a), the chiral auxiliary is (4S)-4-phenyl-2-oxazolidinone; in step (b) the chiral catalyst is (R)-tetrahydro-1-methyl-3,3-diphenyl-1H,3H-pyrrolo(1,2-c)(1,3,2) oxaza-borolidine; in step (c) the hydroxy protecting agent is chlorotrimethylsilane, the Lewis acid is TiCl$_4$ and the tertiary amine is diisopropylethylamine; and in step (d) the silylating agent is bistrimethylsilyl acetamide and the fluoride ion catalyst cyclizing agent is tetrabutylammonium fluoride trihydrate.

8. A process for preparing a compound represented by the formula

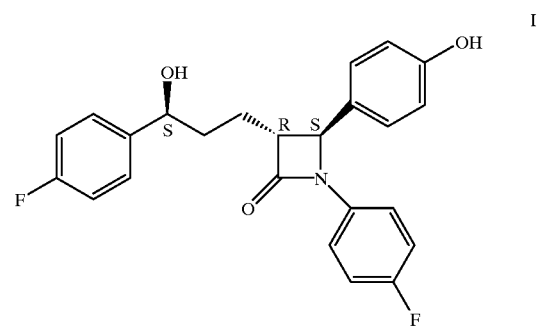

comprising:
  reacting a chiral alcohol of formula V, an imine of formula VI and a hydroxy protecting agent, then condensing the hydroxy-protected compounds to obtain a β-(substituted-amino)amide of formula VII, wherein X is —O—, —S— or —N(C₁–C₆ alkyl); Y is =O or =S; and R¹ is C₁–C₆ alkyl, phenyl, naphthyl, substituted phenyl, substituted naphthyl, C₁–C₆ alkoxycarbonyl or benzyl, wherein the substituents on phenyl and naphthyl are 1–3 substituents selected from the group consisting of C₁–C₆ alkyl, phenyl and benzyl; and wherein Prot is a hydroxy protecting group:

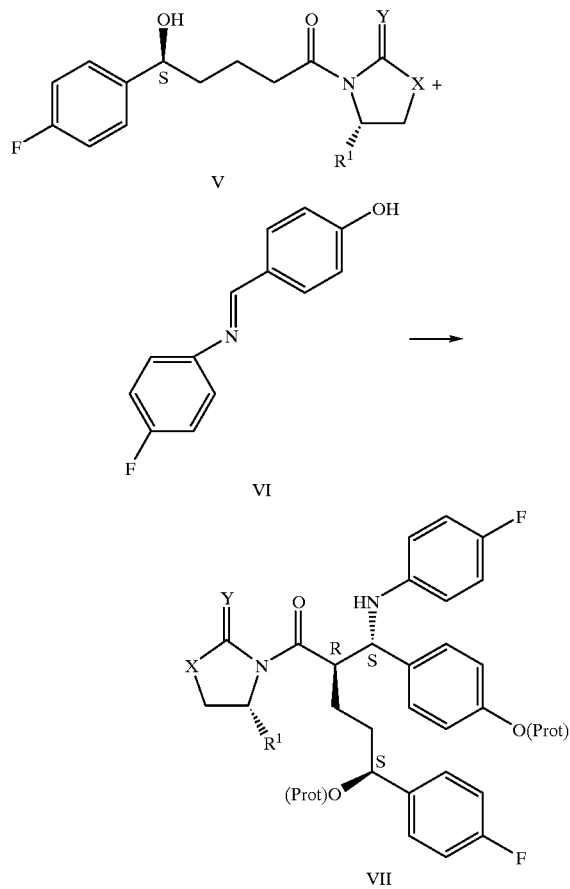

cyclizing the β-(substituted-amino)amide of formula VII with a silylating agent and a fluoride ion catalyst cyclizing agent to obtain the compound of formula VIII:

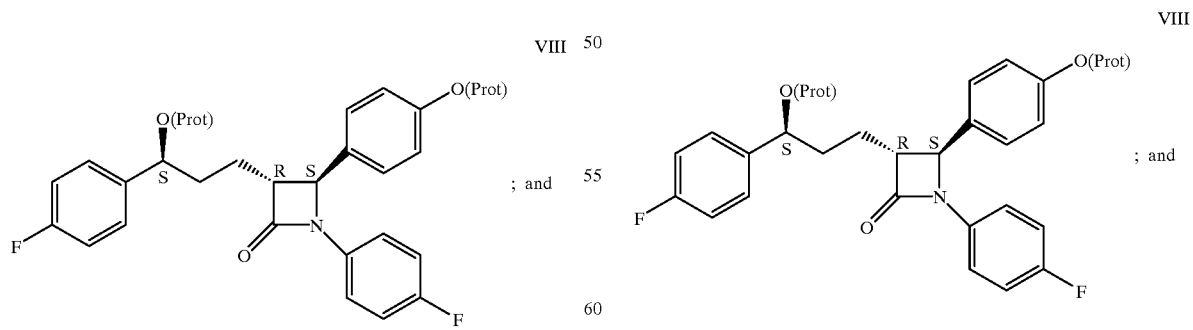

removing the hydroxy protecting groups.

9. A process of claim 8 wherein the the hydroxy protecting agent is chlorotrimethylsilane; the condensation is effected with a Lewis acid in the presence of a tertiary amine; and the silylating agent is bistrimethylsilyl acetamide and the fluoride ion catalyst cyclizing agent is tetrabutylammonium fluoride trihydrate.

10. A process for preparing a compound represented by the formula

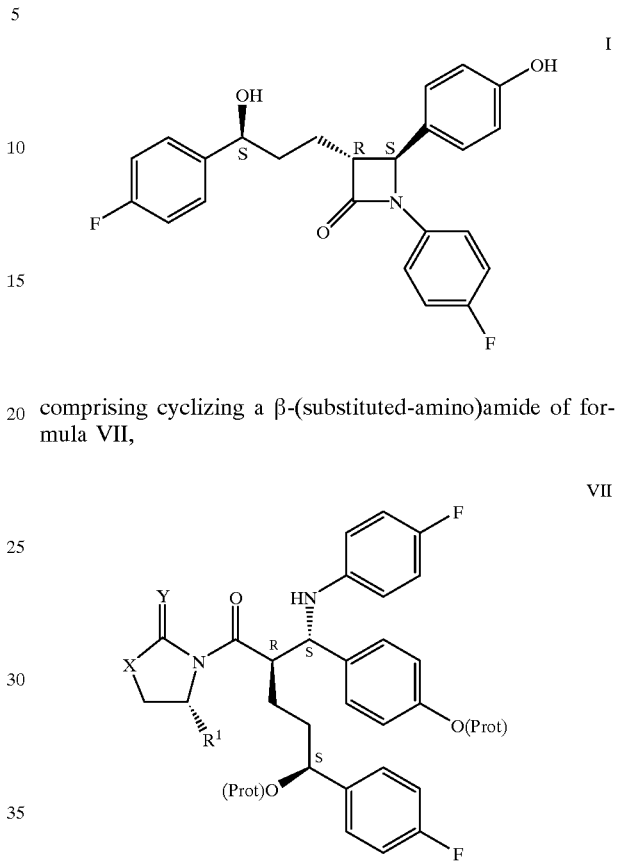

comprising cyclizing a β-(substituted-amino)amide of formula VII, wherein X is —O—, —S— or —N(C₁–C₆ alkyl); Y is =O or =S; and R¹ is C₁–C₆ alkyl, phenyl, naphthyl, substituted phenyl, substituted naphthyl, C₁–C₆ alkoxycarbonyl or benzyl, wherein the substituents on phenyl and naphthyl are 1–3 substituents selected from the group consisting of C₁–C₆ alkyl, phenyl and benzyl; and wherein Prot is a hydroxy protecting group, with a silylating agent and a fluoride ion catalyst cyclizing agent to obtain the compound of formula VIII:

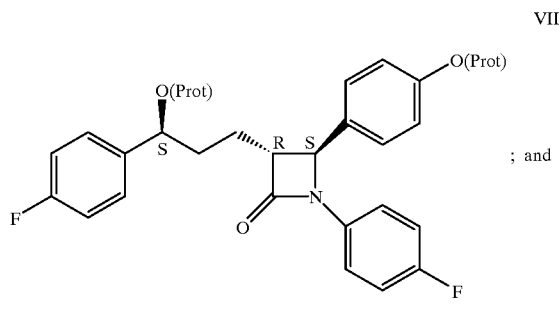

(e) removing the hydroxy protecting groups.

11. A process of claim 10 wherein the silylating agent is bistrimethylsilyl acetamide and the fluoride ion catalyst cyclizing agent is tetrabutylammonium fluoride trihydrate.

12. A process for preparing a β-(substituted-amino)amide of the formula

19

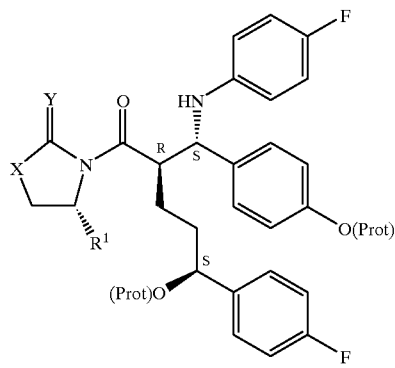

wherein X is —O—, —S— or —N(C$_1$-C$_6$ alkyl); Y is ═O or ═S; and R$^1$ is C$_1$-C$_6$ alkyl, phenyl, naphthyl, substituted phenyl, substituted naphthyl, C$_1$-C$_6$ alkoxycarbonyl or benzyl, wherein the substituents on phenyl and naphthyl are 1–3 substituents selected from the group consisting of C$_1$-C$_6$ alkyl, phenyl and benzyl; and wherein Prot is a hydroxy protecting group, comprising reacting a chiral alcohol of formula V,

V

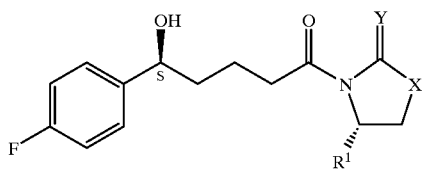

an imine of formula VI

VI

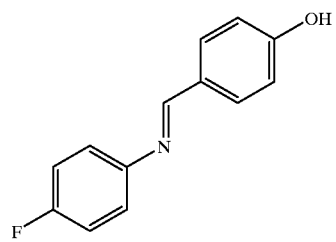

and a hydroxy protecting agent, then condensing the hydroxy-protected compounds to obtain the β-(substituted-amino)amide.

13. The process of claim 11 wherein the hydroxy protecting agent is chlorotrimethylsilane and the condensation is effected with a Lewis acid in the presence of a tertiary amine.

14. A process for preparing a compound of the formula

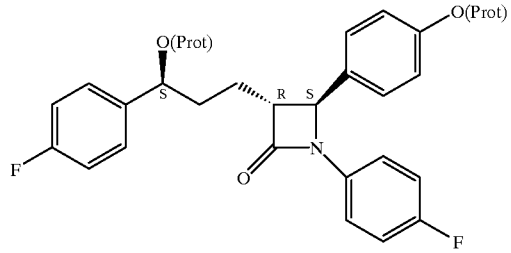

wherein Prot is a hydroxy protecting group, comprising cyclizing β-(substituted-amino)amide of the formula

20

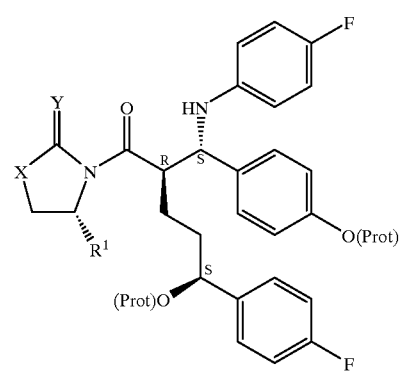

wherein X is —O—, —S— or —N(C$_1$-C$_6$ alkyl); Y is ═O or ═S; and R$^1$ is C$_1$-C$_6$ alkyl, phenyl, naphthyl, substituted phenyl, substituted naphthyl, C$_1$-C$_6$ alkoxycarbonyl or benzyl, wherein the substituents on phenyl and naphthyl are 1–3 substituents selected from the group consisting of C$_1$-C$_6$ alkyl, phenyl and benzyl; and wherein Prot is as defined above, with a silylating agent and a fluoride ion catalyst cyclizing agent.

15. A process of claim 14 wherein the silylating agent is bistrimethylsilyl acetamide and the fluoride ion catalyst cyclizing agent is tetrabutylammonium fluoride trihydrate.

16. A compound of the formula

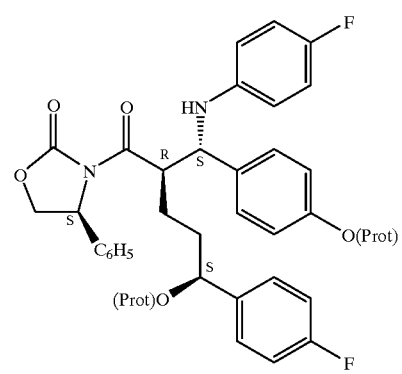

wherein Prot is a hydroxy protecting group.

17. A compound of the formula

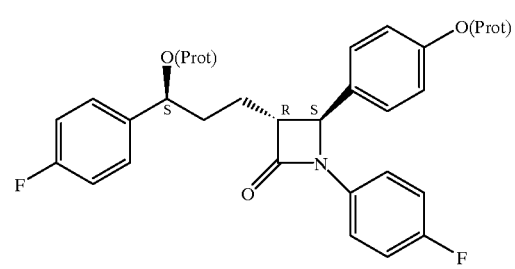

wherein Prot is a hydroxy protecting group.

* * * * *